United States Patent [19]

Murata et al.

[11] 4,197,238

[45] Apr. 8, 1980

[54] METHOD OF PREPARATION OF HUMAN ALBUMIN USING POLYETHYLENE GLYCOL

[75] Inventors: Yorihiko Murata, Amagasaki; Eizo Tsutsui, Hirakata, both of Japan

[73] Assignee: The Green Cross Corporation, Osaka, Japan

[21] Appl. No.: 935,843

[22] Filed: Aug. 22, 1978

Related U.S. Application Data

[63] Continuation of Ser. No. 813,649, Jul. 7, 1977, abandoned.

[30] Foreign Application Priority Data

Apr. 12, 1977 [JP] Japan ..................................... 5241762

[51] Int. Cl.² ............................ C07G 7/00; A23J 1/06
[52] U.S. Cl. .................................. 260/122; 424/101; 424/177
[58] Field of Search .......................................... 260/122

[56] References Cited

U.S. PATENT DOCUMENTS

| 2,705,230 | 3/1955 | Reid | 260/112 B X |
|---|---|---|---|
| 2,765,229 | 10/1956 | Porsche et al. | 260/112 B X |
| 3,415,804 | 12/1968 | Polson | 260/112 B |
| 3,497,492 | 2/1970 | Buck et al. | 260/122 |
| 3,790,552 | 2/1974 | Johnson et al. | 260/112 B |
| 3,869,436 | 3/1975 | Falksveden | 260/112 B |
| 3,926,939 | 12/1975 | Ivanov et al. | 260/112 B X |
| 3,951,937 | 4/1976 | Vnek et al. | 260/112 B |
| 3,992,367 | 11/1976 | Plan et al. | 260/112 B |
| 4,017,470 | 4/1977 | Izaka et al. | 260/122 |

OTHER PUBLICATIONS

Biochim. Biophys. Acta, 82, 463–475 (1964), Polson et al.
Chem. Abstracts, vol. 84, 1976, Schneider et al.
Blut, 30, pp. 121–134 (1975), Schneider et al.

*Primary Examiner*—Howard E. Schain
*Attorney, Agent, or Firm*—Cushman, Darby & Cushman

[57] ABSTRACT

Human albumin free of a blood group substance can simply be prepared by treating an albumin fraction, especially from human placenta with polyethylene glycol to precipitate contaminant proteins containing the blood group substance and recovering albumin from the supernatant fluid.

12 Claims, No Drawings

METHOD OF PREPARATION OF HUMAN ALBUMIN USING POLYETHYLENE GLYCOL

This is a continuation of application Ser. No. 813,649 filed July 7, 1977, now abandoned.

This invention relates to a method for preparing human albumin and, more particularly, to a method for preparing human albumin containing neither a blood group substance (hereinafter referred to as group substance) nor a hypotensive substance.

Recently, a need for transfusion of human albumin, particularly that of a thermostable heat-treated human plasma protein solution containing human albumin has become increasingly important for the treatment of acute hemorrhage, shock, burns, protein malnutrition, hypoproteinemia, etc.

Many methods have been known for recovering purified albumin for infusion from plasma (or serum) derived from human blood. All of the known methods, however, proved to be unsuccessful in economically recovering albumin which is perfectly safe for use in medical treatments, if the starting material contains a large amount of free hemoglobin, in other words, a large amount of red cell walls comprising glycoprotein resolved on hemolysis. Thus, these methods are imperfect or uneconomical in their performance in removing from red cell walls the group substance capable of inducing undesirable side effects. Although placenta is useful as the starting material for production of a fractionated plasma preparation because of its large content of blood and easy availability, yet it contains 50% or more of free hemoglobin caused by the processing of frozen material, the removal of which poses an important problem with respect to the recovery of albumin from the placenta.

The methods so far known for purifying albumin for infusion derived from human blood include:

1. Cohn's sixth procedure of low temperature ethanol fractionation and modification thereof (Japanese Pat. No. 265,704; Japanese Patent Publication No. 5297/60);

2. Method wherein the ionic strength of plasma is decreased by an ion-exchange resin to precipitate the unstable globulin which is then removed [Vox Sanguinis, Vol. 3, p. 184 (1956)];

3. Method consisting in addition of a fatty acid having 12 to 18 carbon atoms to a fractionated blood component solution and heating of the solution at a pH of about 5.2 at about 55° C. to precipitate the unstable globulin which is then removed (Japanese Pat. No. 422,934; Japanese Patent Publication No. 24,895/63);

4. Method which introduces zinc ion into the low temperature ethanol fractionation method [Vox Sanguinis, Vol. 5, p. 272 (1960)];

5. Method for stepwise separation of hemoglobin by combining the ammonium sulfate fractionation with the low temperature ethanol fractionation (Japanese Patent Publication No. 2869/72);

6. Method involving addition of butyric acid to a fractionated blood component solution and heating of the solution at a pH of about 5.0 at about 60° C. to precipitate hemoglobin along with unstable globulin which are then removed (Japanese Pat. No. 534,921; Japanese Patent Publication No. 16,041/68);

7. Method which comprises adding mandelic acid to a fractionated blood component solution and heating the solution at a pH of about 4.9 at about 60° C. to precipitate unstable globulin together with hemoglobin which are then removed (Japanese patent application "Kokai" (Laid-open) No. 66,810/74];

8. Method comprising addition of trichloroacetic acid at an ethanol concentration of 55% or more based on total amount of the solution and at a temperature of $-5°$ to $-10°$ C. to remove the group substance [Japanese patent application "Kokai" (Laid-open) Nos. 85,218/74 and 85,219/74].

The first, second, and third methods are not applicable to a blood such as placental blood which has undergone hemolysis and contains large amounts of liberated hemoglobin and group substance, because these methods have no specific effects on precipitation of hemoglobin as well as the group substance and, accordingly, separation of albumin from hemoglobin and group substance is insufficient.

The fourth and fifth methods are not only uneconomical because of complicated operational conditions of each step and, hence, complicated fractionation procedure, but also difficult to carry out because of the employment of flammable alcohol and the necessary cooling to maintain a low temperature.

The six and seventh methods permit of entire treatment at an ordinary temperature, are easy to operate in removing hemoglobin from a human plasma such as a placental extract containing a large amount of hemoglobin, and is economical, but the removal of group substance is impossible by these methods.

The eighth method adopts a measure to remove hemoglobin and group substance, but bears a danger of protein denaturation due to trichloroacetic acid which is a protein denaturant (precipitant); the method has also a difficulty in safety of operation because of the employment of inflammable alcohol at a high concentration and is uneconomical on account of continual cooling required to maintain a low temperature of $-5°$ to $-10°$ C.

An object of this invention is to provide an economical and safe procedure for recovering albumin from the human blood, particularly the human blood containing liberated hemoglobin.

As a result of studies conducted on the recovery of human plasma protein comprising albumin as major component from a human blood, the present inventors found a simple and safe method. By combining said finding with prior art, it has been possible to accomplish the present invention relating to an economical method for recovering human plasma protein containing albumin as major component which is safely usable in medical treatments.

According to the present invention, there is provided a method for preparing human albumin, which comprises treating an aqueous solution of albumin of human origin containing blood group substance with polyethylene glycol to precipitate contaminant protein containing said group substance.

The aqueous solution of albumin of the human origin containing group substance for use as the starting material can be either highly purified one or that in an earlier stage of purification. Such an albumin solution is obtained by removing globulin, hemoglobin and alkaline phosphatase from plasma or serum of human and contains albumin in an amount of at least 50%, preferably 80% on the total protein contained. Any of the aqueous solutions which have undergone partial hemolysis and containing albumin, as major constituent, and group substance together with hypotensive substances is suitable, whether it has been obtained from blood, placental extract, retroplacental blood, or plasma derived from human blood. A desirable procedure for the pretreatment consists in that in order to remove hemoglobin and alkaline phosphatase, an aqueous solution of plasma protein, which has been freed from γ-globulin, is heated at 50° to 65° C. in the presence of 2 to 6% (W/V) of butyric acid or mandelic acid and 0.5 to 1.5 mM of ethylenediaminetetraacetic acid (EDTA), preferably disodium salt of EDTA, under a pH condition of 4.5 to 5.5. After removing the resultant precipitate, the supernatant is ready for use.

Polyethylene glycol suitable for use has a molecular weight of generally 2,000 to 10,000, although those having a molecular weight of 4,000 to 8,000 are most effective. When polyethylene glycol is added to an aqueous solution of albumin used as starting material, there is formed a precipitate. Although depending upon the nature of the aqueous solution used as starting material, the effective final concentration of polyethylene glycol in the aqueous solution is generally 10 to 30% (W/V), though ca. 50% (W/V)-aqueous solution can be used if there is surplus treating capacity of the reactor. A desirable condition is 13 to 20% (W/V) in a pH range of 6.6 to 8.0 and 15 to 30% (W/V) in a pH range of 8.0 to 9.6. It is effective to adjust the protein concentration in the reactant solution to 5 to 40 g/liter. The concentration of an inorganic salt is preferably adjusted to 50 g/liter or less in terms of sodium chloride. The reaction temperature can be selected from a wide range of 2° to 30° C. without requiring exceedingly intensive cooling. However, as a general precaution in dealing with a protein solution, it is desirable to carry out the reaction at a low temperature as far as possible within the above range.

By the above treatment, albumin is scarcely precipitated whereas the group substance comprising glycoprotein is precipitated. If contaminant proteins such as hemoglobin, a hypotensive substance comprising peptides of low molecular weights of 1,000 to 10,000, and the like are present, they are precipitated along with the group substance and are removed from the aqueous albumin solution.

The conditions for the above procedure of removing the group substance can be determined by conducting comparative experiments on the relationships among molecular weight and final concentration of polyethylene glycol and pH of the reactant mixture. As an example, in treating a starting aqueous albumin solution containing each 1% (W/V) of proteins and a salt (in terms of sodium chloride) with polyethylene glycol having an average molecular weight of 4,000 or 8,000, the amount added of polyethylene glycol and pH of the reactant mixture were varied to obtain the results of group substance removal as shown in Table 1.

Determination of the group substance was performed by use of blood-group specific antiserum following the method or its slightly modification of hemagglutination inhibition test [E. A. Kabat, M. M. Meyer, Experimental Immunochemistry, Vol. 2, pp. 97–132 (1961)] and the results were expressed as the minimum amount (maximum dilution ratio) of antiserum causing agglutination of erythrocytes at which the antiserum is capable of completely neutralizing the group substance contained in the sample and still agglutinizing the erythrocyte.

The denotation of "% (W/V)" in this specification and claims shows the concentration of a solute in a solution in the proportion of the solute in weight unit and the solution in volume unit.

| Average molecular weight of polyethylene glycol | Concentration of polyethylene glycol in reactant solution, % (W/V) | pH of reactant solution | Dilution ratio of blood-group antiserum showing effectiveness of group substance removal |
|---|---|---|---|
| 4,000 | 10 | 5 | x 64 |
| | | 7 | x 128 |
| | | 9 | x 64 |
| | | 10 | x 64 |
| | 20 | 5 | x 64 |
| | | 7 | x 256 |
| | | 9 | x 256 |
| | | 10 | x 128 |
| | 30 | 5 | x 64 |
| | | 7 | x 256 |
| | | 9 | x 256 |
| | | 10 | x 128 |
| | 35 | 5 | x 16 |
| | | 7 | x 64 |
| | | 9 | x 124 |
| | | 10 | x 128 |
| 8,000 | 10 | 5 | x 64 |
| | | 7 | x 128 |
| | | 9 | x 64 |
| | | 10 | x 64 |
| | 20 | 5 | x 128 |
| | | 7 | x 256 |
| | | 9 | x 256 |
| | | 10 | x 256 |
| | 30 | 5 | x 32 |
| | | 7 | x 256 |
| | | 9 | x 256 |
| | | 10 | x 128 |
| | 35 | 5 | x 32 |
| | | 7 | x 128 |
| | | 9 | x 128 |
| | | 10 | x 128 |
| Untreated starting material | | | x 4 |
| Normal saline solution | | | x 256 |

After removal of the contaminant proteins in the form of precipitate, the supernatant is fractionated to recover albumin. Since almost all the contaminant proteins have been removed, the recovery of albumin requires no specific technique, but is effected by precipitating all of the proteins by well-known ammonium sulfate fractionation or alcohol fractionation. A preferable procedure is to utilize the method of polyethylene glycol fractionation.

An efficient recovery of the albumin fraction can be achieved by using polyethylene glycol under an acidic condition, preferably at pH 4.5 to 5.6, and at its final concentration of 20 to 30% (W/V). Thus, recovery of albumin from the supernatant can be conveniently accomplished by simply adding, if necessary, an additional amount of polyethylene glycol to keep pH of the supernatant within the above range.

A plasma protein without having a danger of hepatitis virus infection can be prepared by inclusion of a procedural step of the customary heat treatment of the thus obtained albumin fraction at 60° C. for 10 hours in the presence of a suitable stabilizer.

It is desirable for the medical use that the albumin finally obtained in the form of precipitate be subjected to dialysis to remove the salts and then to filtration of bacteria. Reduction in the polyethylene glycol content can be achieved by washing the precipitate with distilled water having a pH in the acidic range and containing polyethylene glycol in a low concentration. Thus, an albumin protein containing little polyethylene glycol may be obtained. If necessary, the albumin protein can be further subjected to electrodialysis with desirable result. Thereafter, the product is dehydrated in a suitable way to obtain a dry reference standard preparation.

The surprising advantages of the present invention are removal of not only the group substance, but also the reduction of the hypotensive substance and that of the pyrogenic substance which may occasionally be accompanied by in the starting material. These impurities are also included in the precipitate formed on addition of polyethylene glycol and are removed therewith.

On analysis by the electrophoretic method [T. Kawai and N. Aoki, "Fractionation of serum proteins by cellulose acetate electrophoresis," p. 35 (Yagi Publishing Co., Tokyo, 1972)], the albumin reference standard showed a protein composition composed of 95 to 98% of albumin and 2 to 5% of $\alpha$-globulin and $\beta$-globulin. When analyzed by the ultracentrifugal method [T. Isemura et al., J. Biochem., Vol. 44, p. 443 (1957)], it showed single peak which indicates that it is a pure protein. The group substance content was estimated by the method of the hemagglutination inhibition test by use of blood-group specific antiserum (loc. cit.). It was found that the group substance had been removed to a degree comparable to that in normal saline solution, as measured by the dilution rato of antiserum (see Table 1). The hypotensive substance content was evaluated by administering a sample preparation to an adult dog and measuring the percentage depression of blood pressure against the arterial pressure before administration. The percentage depression was found to be 10% or less, indicating that the sample is sufficiently free from the hypotensive substance for medical use.

As mentioned in the foregoing, according to this invention, the group substance may be removed completely and economically and, at the same time, the hypotensive substance is also removed. There is thus provided, with a high efficiency, a plasma protein comprising major amount of albumin without having a fear for side effects due to the presence of above-noted contaminants. By combining the present method with conventional techniques for preparing albumin, there is provided a way of supplying albumin infusion preparations, which contributes much to the medical treatment.

The invention is illustrated below with reference to Examples, but the invention is not limited to these examples.

EXAMPLE 1

Expelled placentas were immediately enclosed in a clean plastic bag and frozen for storage in a low temperature refrigerator at $-20°$ C. Such frozen placentas were collected from hospitals and maternity hospitals. Plastic bags containing 1,000 frozen placentas were externally washed with pyrogen-free distilled water and coarsely crushed by means of an ice crusher. The plastic bag was easily removed. The coarsely crushed frozen placentas were finely crushed to a minced meat stage by means of a meat chopper.

To about 600 kg of the finely crushed placentas, was added 700 liters of 1%-saline water. The mixture was agitated at a temperature below 12° C. for 45 minutes to extract the blood component. The extract was centrifuged to remove the placental residues and to separate the supernatant solution (placenta extract). With respect to proteins, the placenta extract contained 3.5% of total protein, 2.3% of hemoglobin, and 1.2% of other plasma proteins.

To 1 liter of the above extract, was added 285 g of ammonium sulfate and the resulting precipitate containing $\gamma$-globulin was removed. Hemoglobin, most part of group substance, and albumin were remained in the supernatant layer. Since the protein concentration in the supernatant was small, total protein was collected in the form of precipitate by adding to the supernatant 200 g per liter of ammonium sulfate and adjusting pH to 6–7. The precipitate was dehydrated as far as possible and dissolved in pyrogen-free distilled water in a proportion of 4 to 7 liters per kg of the precipitate. Regardless of the amount, the ammonium sulfate which had been adhered to the protein during the above pretreatment and carried by the protein had no effect on the subsequent treatments. The solution thus obtained was admixed, while stirring, with mandelic acid in a customary way until the final concentration of the latter became 4%. While maintaining pH between 4.9 and 5.0, the solution was kept at 58° to 60° C. for about 1 hour to precipitate exhaustively the thermolabile proteins. By this treatment most part of hemoglobin was removed along with the thermolabile globulin, whereas the developed activity of group substance, hypotensive substances, and albumin passed into the supernatnat. The protein in the supernatant contained 1.5% of albumin. In order to remove the group substance and hypotensive substances, the supernatant was adjusted to a protein concentration of 5 to 40 g/liter and a salt concentration of 5% or less in terms of sodium chloride. To the resulting supernatant, was added 220 g of solid polyethylene glycol having an average molecular weight of 6,000 per 1,000 ml of the supernatant and pH was adjusted to make the supernatant 8.0 to precipitate some proteins. The precipitate was removed, leaving behind a supernatant containing only protein component comprising the objective albumin as major constituent.

Since the protein concentration in the above supernatant was small, the proteins contained in the supernatant were collected again in the form of precipitate by simply adjusting pH to the acidic side. When polyethylene glycol was contained in a concentration of 20% or more, the desired protein was precipitated by simply adjusting pH of the supernatant to 4.5 to 5.6. The precipitate was separated by dehydration and there was obtained purified plasma protein comprising, as major constituent, albumin contaminated with neither group substance nor hypotensive substances.

The precipitate thus obtained was dissolved in pyrogen-free distilled water and analyzed electrophoretically. The protein was found to be of the following composition: 95–98% of albumin and 2–5% of $\alpha$-globulin and $\beta$-globulin. On analysis of ultracentrifuging, the protein showed single peak of albumin, which is indicative of a pure protein.

The above pure protein did not show any sign of denaturation such as formation of precipitate or appearance of turbidity. It showed no toxicity when administered to mouse, guinea pig, rabbit, or dog and had no undesirable properties such as development of the activity of group substance and hypertensive effect.

The yield of plasma protein thus obtained was 2.3 g per placenta.

EXAMPLE 2

Following the procedure used in Example 1 for treating the placental extract, pure plasma protein comprising albumin as major constituent could be obtained also from the serum contained in retroplacental blood used as starting materal or from venous blood which had undergone hemolysis, also used as starting material. The yield was about 11 g and 17 g from each 1 liter of the retroplacental serum and the serum of venous blood with hemolysis, respectively.

EXAMPLE 3

The treating procedure of Example 1 was repeated, except that EDTA was added to the solution to a final concentration of 1 mM in the step wherein mandelic acid was added to the solution to a final concentration of 4% and the solution is heated at 58°-60° C. for about 1 hour while maintaining pH of the solution within the acidic range (pH 4.5-5.5). The plasma protein comprising albumin as major constituent was completely free from not only group substance, hypotensive substances, and hemoglobin, but also alkaline phosphatase.

The enzymatic activity of the alkaline phosphatase was estimated by the method described in Journal of Biological Chemistry, Vol. 164, p. 321 (1946).

What is claimed is:

1. A method for removing a blood group substance from an aqueous solution of human albumin, said method comprising treating an aqueous solution of albumin of human origin free from gamma-globulin and containing a blood-group substance and hypotensive substance with polyethylene glycol at pH of 6.6 to 8.0 the effective polyethylene glycol concentration in the aqueous albumin solution of 13 to 20% (w/v) in the presence of an inorganic salt at a concentration of at most 50 g/liter measured as sodium chloride and at a temperature in the range of 2° C. to 30° C., the resulting polyethylene glycol/albumin solution having a protein concentration of 5 to 40 g/liter, thereby precipitating and removing contaminant proteins containing said blood-group substance and recovering albumin from the supernatant fluid.

2. A method according to claim 1 wherein the aqueous solution of albumin contains at leat 50% of albumin based on the total protein and the aqueous solution of albumin is originated from human placenta or human retroplacental blood and the polyethylene glycol has an average molecular weight of 2,000 to 10,000.

3. A method according to claim 1 including the steps of adjusting the supernatant fluid to a pH of 4.5 to 5.6 and to a polyethylene glycol concentration of 20 to 30% (w/v) to precipitate albumin and then recovering albumin therefrom.

4. A method according to claim 3 wherein the original aqueous solution of albumin contains at least 50% of albumin based on the total protein and the aqueous solution of albumin is originated from human placenta or human retroplacental blood and the polyethylene glycol has an average molecular weight of 2,000 to 10,000.

5. A method for removing a blood group substance from an aqueous solution of human albumin, said method comprising treating an aqueous solution of albumin of human origin free from gamma-globulin and containing a blood-group substance and hypotensive substance with polyethylene glycol at pH of 8.0 to 9.6, the effective polyethylene glycol concentration in the aqueous albumin solution of 15 to 30% (w/v), in the presence of an inorganic salt at a concentration of at most 50 g/liter measured as sodium chloride and at a temperature in the range of 2° C. to 30° C. the resulting polyethylene glycol/albumin solution having a protein concentration of 5 to 40 g/liter, thereby precipitating and removing contaminant proteins containing said blood-group substance and recovering albumin from the supernatant fluid.

6. A method according to claim 5 wherein the aqueous solution of albumin contains at least 50% of albumin based on the total protein and the aqueous solution of albumin is originated from human placenta or human retroplacental blood and the polyethylene glycol has an average molecular weight of 2,000 to 10,000.

7. A method according to claim 5 including the steps of adjusting the supernatant fluid to a pH of 4.5 to 5.6 and to a polyethylene glycol concentration of 20 to 30% (w/v) to precipitate albumin and then recovering albumin therefrom.

8. A method according to claim 7 wherein the original aqueous solution of albumin contains at least 50% of albumin based on the total protein and the aqueous solution of albumin is originated from human placenta or human retroplacental blood and the polyethylene glycol has an average molecular weight of 2,000 to 10,000.

9. A method for removing a blood group substance from an aqueous solution of human albumin containing at least 50% of the albumin, based on the total protein, the aqueous solution originating from human placenta or human retroplacental blood, said method comprising
  (1) treating an aqueous solution of albumin of human origin containing a blood-group substance free from gamma-globulin, and hypotensive substance with polyethylene glycol having an average molecular weight in the range of 2,000 to 10,000 and at pH of 6.6 to 9.6 at a polyethylene glycol concentration of 13 to 30% (w/v) to the aqueous solution of albumin having a protein concentration of 5 to 40 g/liter, an inorganic salt concentration of at most 50 g/liter, measured as sodium chloride, and at a temperature in the range of 2° C. to 30° C.; and
  (2) precipitating and substantially removing contaminant proteins containing said blood-group substance and said hypotensive substance and
  (3) recovering human albumin from the supernatant fluid.

10. A method according to claim 1, wherein the aqueous solution of albumin is originated from human placenta or human retroplacental blood.

11. A method according to claim 1, wherein the aqueous solution of albumin contains at least 50% of albumin on the total protein contained.

12. A method according to claim 1, wherein the polyethylene glycol has an average molecular weight of 2,000 to 10,000.

* * * * *